United States Patent
Ni et al.

(10) Patent No.: US 12,123,029 B2
(45) Date of Patent: Oct. 22, 2024

(54) CYCLOHEXENECARBOXYLATE ESTER HYDROLASE, AND MUTANT, CODING GENE, EXPRESSION VECTOR, RECOMBINANT BACTERIUM AND USE THEREOF

(71) Applicant: JIANGNAN UNIVERSITY, Wuxi (CN)

(72) Inventors: Ye Ni, Wuxi (CN); Zhe Dou, Wuxi (CN); Guochao Xu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 491 days.

(21) Appl. No.: 17/296,218

(22) PCT Filed: Jul. 30, 2020

(86) PCT No.: PCT/CN2020/105687
§ 371 (c)(1),
(2) Date: May 21, 2021

(87) PCT Pub. No.: WO2022/106597
PCT Pub. Date: Jan. 27, 2022

(65) Prior Publication Data
US 2022/0396781 A1 Dec. 15, 2022

(30) Foreign Application Priority Data
Jul. 23, 2020 (CN) .......................... 202010719130.6

(51) Int. Cl.
*C12N 9/18* (2006.01)
*C07C 51/09* (2006.01)
*C12N 15/70* (2006.01)
(52) U.S. Cl.
CPC ................ *C12N 9/18* (2013.01); *C07C 51/09* (2013.01); *C12N 15/70* (2013.01)

(58) Field of Classification Search
CPC .................................. C12N 9/18; C07C 51/09
See application file for complete search history.

(56) References Cited

FOREIGN PATENT DOCUMENTS

| CN | 1408848 A | 4/2003 |
| CN | 106119303 A | 11/2016 |
| CN | 110272839 A | 9/2019 |

OTHER PUBLICATIONS

GenBank: PZQ90293.1; https://www.ncbi.nlm.nih.gov/protein/PZQ90293.1?report=genbank&log$=protalign&blast_rank=2&RID=V5HTMN4N016; accessed Jan. 25, 2004 (Year: 2018).*
(Continued)

*Primary Examiner* — Louise W Humphrey
*Assistant Examiner* — Candice Lee Swift
(74) *Attorney, Agent, or Firm* — SZDC Law PC (57) ABSTRACT

The present invention discloses a cyclohexenecarboxylate ester hydrolase, and a mutant, a coding gene, an expression vector, recombinant bacterium and use thereof. The cyclohexenecarboxylate ester hydrolase AcEst1 and its mutant of the present invention have the function of enantioselectively resolving methyl 3-cyclohexene-1-carboxylate with high efficiency to prepare optically active (S)-3-cyclohexene-1-carboxylic acid. When the substrate concentration is as high as 2000 mM (about 280 g/L), the optical purity of the product is higher than 99%, and the substrate/catalyst is as high as 3500 g/g. As compared with other preparation methods, the product prepared by the method of the present invention has high concentration and high optical purity, the catalytic efficiency is high, the reaction conditions are mild. Furthermore, the method is environmentally friendly, simple in operation and easy for industrial scale-up, thus has a good prospect of application in industry.

8 Claims, 1 Drawing Sheet
Specification includes a Sequence Listing.

(56) References Cited

OTHER PUBLICATIONS

Fassler J, Cooper P. Blast Glossary. Jul. 1, 20114. In: BLAST® Help [Internet]. Bethesda (MD): National Center for Biotechnology Information (US); 2008—. Available from: https://www.ncbi.nlm.nih.gov/books/NBK62051/ (Year: 2008).*

Pesaresi, Alessandro, and Doriano Lamba. "Insights into the fatty acid chain length specificity of the carboxylesterase PA3859 from Pseudomonas aeruginosa: A combined structural, biochemical and computational study." Biochimie 92.12 (2010): 1787-1792. (Year: 2010).*

Yin, Jin-Gang, et al. "Cloning and characterization of an enantioselective l-menthyl benzoate hydrolase from Acinetobacter sp. ECU2040." Applied biochemistry and biotechnology 176 (2015): 1102-1113. (Year: 2015).*

Day, J. N. E., and C. K. Ingold. "Mechanism and kinetics of carboxylic ester hydrolysis and carboxyl esterification." Transactions of the Faraday Society 37 (1941): 686-705. (Year: 1941).*

MetaCyc; https://biocyc.org/META/NEW-IMAGE?object=CARBOXYLESTERASE-RXN; accessed Mar. 28, 2024 (Year: 2012).*

GenBank; https://www.ncbi.nlm.nih.gov/protein/AIK29633.1/; accessed Mar. 28, 2024 (Year: 2013).*

Sood, S., et al. "Carboxylesterases: sources, characterization and broader applications." Insight Enzym Res 1.1 (2016): 1-11. (Year: 2016).*

Tanyeli et al., "Enzyme catalyzed reverse enantiomeric separation of methyl (±)-3-cyclohexene-1-carboxylate" Tetrahedron: Asymmetry 15 (2004) 2057-2060 (Dec. 31, 2004).

Dou et al., "A novel carboxylesterase from Acinetobacter sp. JNU9335 for efficient biosynthesis of Edoxaban precursor with high substrate to catalyst ratio" Bioresource Technology 317 (2020) 123984 (Dec. 31, 2020).

Wu et al., "Improved enantioselectivity of E. coli BioH in kinetic resolution of methyl (S)-3-cyclohexene-1-carboxylate by combinatorial modulation of steric and aromatic interactions" Bioscience, Biotechnology, and Biochemistry 2019, vol. 83, No. 7, 1263-1269 (Apr. 2, 2019).

Kim et al., "Gene Cloning, Sequencing, and Expression of an Esterase from Acinetobacter lwoffii 16C-1" Current Microbiology vol. 46 (2003), pp. 291-295 (Dec. 31, 2003).

Xu et al., "Chiral resolution of cyclohex-3-ene-1-carboxylic acid" Drug & Clinic, vol. 28, No. 2, pp. 126-128 (Mar. 31, 2013).

Brooks, B. et al., esterase [Acinetobacter johnsonii], GenBank: PZQ90293.1 (Jun. 18, 2018).

* cited by examiner

SEQUENCE LISTING

```
<160> NUMBER OF SEQ ID NOS: 8

<210> SEQ ID NO 1
<211> LENGTH: 1074
<212> TYPE: DNA
<213> ORGANISM: Artificial sequence
<220> FEATURE:
<223> OTHER INFORMATION: Cyclohexenecarboxylate ester hydrolase

<400> SEQUENCE: 1
atgggcgtgt tgaatcaaac tttacaacaa tggatggaac aaggccaagg cagtgcggca      60
cgattaattg atcgcttacc gacagtagca caagaaggct tggtgaaagc gctgggttat     120
cctcaccagt ttgaacaact ggacccettt attaaatgct taatggcggc tcaatataag     180
caaggcaaat cgggctttat ttttgaagac taccatcgtt cgcgtaaatt gtttgatcat     240
caaattcaaa tgttgaccgc caaacccagc gcgataaaac aagtggaaga tttacgtcta     300
cctttacaaa gtggaactgt gtttgcacgg cattatcatc ctgcaccgaa taagaaactt     360
ccgatgctgg tgtttttatca tggcggcggc tttgtggttg gcagcctcga cagccatgat     420
gaagtctgtc gcttacttgc aatccatgcc aaagtgcagg tgctcagtat tgactatcct     480
ttggcgccag aagttggccc gaatgtactg attcaatctt gtgaagatgc tttggcttgg     540
gtctatcaaa accgtcgtca gttcaaaatt ttgaaaaacc gaattgcggt ggctggcgat     600
agtgcaggtg gtaatatcag tgccgtagtg gcgcagcgaa ctgctgcaaa agcttatgcg     660
ccaagtgcac aactgttaat ttaccccgtg gtcgatttca aaagtcgcca tccatcgttc     720
tttgcttata aggatggact gaccttaact gggcaagatt tgatagggt gacatcgttg     780 tatgctgaac aacatcaagt ggctttagat aatcctattg tttcgccaac ctacggcgta     840
ttaaaaagta tcgctcccgc ttttgtcatc accgcaggtc atgatttatt gcatgatgaa     900
ggtgaaattt acgccatcaa attaaagcag cagggtaata aggtttatta tcagaattat     960
ctagatcaac cccatgggtt tgtgaacttc accatcattt ctcgtcgagc aaaaaaaatc    1020
accatagaaa tggcaaagag ctttagaaaa ttttgggata agaatgccaa ataa         1074

<210> SEQ ID NO 2
<211> LENGTH: 357
<212> TYPE: PRT
<213> ORGANISM: Artificial sequence
<220> FEATURE:
<223> OTHER INFORMATION: Cyclohexenecarboxylate ester hydrolase
```

-continued

<400> SEQUENCE: 2

Met Gly Val Leu Asn Gln Thr Leu Gln Gln Trp Met Glu Gln Gly Gln
1               5                   10                  15

Gly Ser Ala Ala Arg Leu Ile Asp Arg Leu Pro Thr Val Ala Gln Glu
            20                  25                  30

Gly Leu Val Lys Ala Leu Gly Tyr Pro His Gln Phe Glu Gln Leu Asp
        35                  40                  45

Pro Phe Ile Lys Cys Leu Met Ala Ala Gln Tyr Lys Gln Gly Lys Ser
50                  55                  60

Gly Phe Ile Phe Glu Asp Tyr His Arg Ser Arg Lys Leu Phe Asp His
65                  70                  75                  80

Gln Ile Gln Met Leu Thr Ala Lys Pro Ser Ala Ile Lys Gln Val Glu
                85                  90                  95

Asp Leu Arg Leu Pro Leu Gln Ser Gly Thr Val Phe Ala Arg His Tyr
            100                 105                 110

His Pro Ala Pro Asn Lys Lys Leu Pro Met Leu Val Phe Tyr His Gly
        115                 120                 125

Gly Gly Phe Val Val Gly Ser Leu Asp Ser His Asp Glu Val Cys Arg
    130                 135                 140

Leu Leu Ala Ile His Ala Lys Val Gln Val Leu Ser Ile Asp Tyr Pro
145                 150                 155                 160

Leu Ala Pro Glu Val Gly Pro Asn Val Leu Ile Gln Ser Cys Glu Asp
                165                 170                 175

Ala Leu Ala Trp Val Tyr Gln Asn Arg Arg Gln Phe Lys Ile Leu Lys
            180                 185                 190

Asn Arg Ile Ala Val Ala Gly Asp Ser Ala Gly Gly Asn Ile Ser Ala
        195                 200                 205

Val Val Ala Gln Arg Thr Ala Ala Lys Ala Tyr Ala Pro Ser Ala Gln
    210                 215                 220

Leu Leu Ile Tyr Pro Val Val Asp Phe Lys Ser Arg His Pro Ser Phe
225                 230                 235                 240

Phe Ala Tyr Lys Asp Gly Leu Thr Leu Thr Gly Gln Asp Val Asp Arg
                245                 250                 255

Val Thr Ser Leu Tyr Ala Glu Gln His Gln Val Ala Leu Asp Asn Pro
            260                 265                 270

Ile Val Ser Pro Thr Tyr Gly Val Leu Lys Ser Ile Ala Pro Ala Phe
        275                 280                 285

Val Ile Thr Ala Gly His Asp Leu Leu His Asp Glu Gly Glu Ile Tyr
    290                 295                 300

Ala Ile Lys Leu Lys Gln Gln Gly Asn Lys Val Tyr Tyr Gln Asn Tyr
305                 310                 315                 320

Leu Asp Gln Pro His Gly Phe Val Asn Phe Thr Ile Ser Arg Arg
                325                 330                 335

Ala Lys Lys Ile Thr Ile Glu Met Ala Lys Ser Phe Arg Lys Phe Trp
            340                 345                 350

Asp Lys Asn Ala Lys
        355

<210> SEQ ID NO 3
<211> LENGTH: 43
<212> TYPE: DNA
<213> ORGANISM: Artificial sequence
<220> FEATURE:
<223> OTHER INFORMATION: Primer

```
<400> SEQUENCE: 3
gtgccgcgcg gcagccatat gatgggcgtg ttgaatcaaa ctt          43

<210> SEQ ID NO 4
<211> LENGTH: 45
<212> TYPE: DNA
<213> ORGANISM: Artificial sequence
<220> FEATURE:
<223> OTHER INFORMATION: Primer

<400> SEQUENCE: 4
gtggtggtgg tggtgctcga gttatttggc attcttatcc caaaa        45

<210> SEQ ID NO 5
<211> LENGTH: 43
<212> TYPE: DNA
<213> ORGANISM: Artificial sequence
<220> FEATURE:
<223> OTHER INFORMATION: Primer

<400> SEQUENCE: 5
gtgccgcgcg gcagccatat gatgggcgtg ttgaatcaaa ctt          43

<210> SEQ ID NO 6
<211> LENGTH: 45
<212> TYPE: DNA
<213> ORGANISM: Artificial sequence
<220> FEATURE:
<223> OTHER INFORMATION: Primer

<400> SEQUENCE: 6
gtggtggtgg tggtgctcga gttatttggc attcttatcc caaaa        45

<210> SEQ ID NO 7
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: MUTAGEN
<222> LOCATION: (13)..(13)
<223> OTHER INFORMATION: n is a, c, g, or t

<400> SEQUENCE: 7
tcgcgtaaat tgndtgatca tcaaatt                            27

<210> SEQ ID NO 8
<211> LENGTH: 27
<212> TYPE: DNA
<213> ORGANISM: Artificial sequence
<220> FEATURE:
<223> OTHER INFORMATION: Primer
<220> FEATURE:
<221> NAME/KEY: MUTAGEN
<222> LOCATION: (15)..(15)
<223> OTHER INFORMATION: n is a, c, g, or t

<400> SEQUENCE: 8
aatttgatga tcahncaatt tacgcga                            27
```

CYCLOHEXENECARBOXYLATE ESTER HYDROLASE, AND MUTANT, CODING GENE, EXPRESSION VECTOR, RECOMBINANT BACTERIUM AND USE THEREOF This application is the National Stage Application of PCT/CN2020/105687, filed on Jul. 30, 2020, which claims priority to Chinese Patent Application No. 202010719130.6, filed on Jul. 23, 2020, which is incorporated by reference for all purposes as if fully set forth herein.

FIELD OF THE INVENTION

The present invention relates to the technical field of genetic engineering, and more particularly to a cyclohexenecarboxylate ester hydrolase, and a mutant, a coding gene, an expression vector, a recombinant bacterium and use thereof.

DESCRIPTION OF THE RELATED ART (S)-3-cyclohexene-1-carboxylic acid [(S)-CHCA]: molecular formula $C_7H_{10}O_2$, molecular weight 126.15, melting point 118° C./6 mmHg(lit.), and CAS No.: 5708-19-0.

Chiral 3-cyclohexene-1-carboxylic acid is an important building block for the construction of a variety of natural products, chiral drugs and agrochemicals. It can be used to synthesize many natural products and drugs, such as the new immunosuppressant tacrolimus, the anti-tumor drug (+)-Phyllanthocin, the attractant (−)-perlapine-B for insect control, the neuraminidase inhibitor oseltamivir phosphate, and the coagulation factor Xa inhibitor edoxaban, etc. With the continuous expansion of chiral drug market, the demand for chiral cyclohexene-1-carboxylic acid grows rapidly. The unsaturated six-membered ring in 3-cyclohexene-1-carboxylic acid is highly symmetric, and the difference between the groups on both sides of the chiral carbon is very small, causing a great challenge to its high enantioselective synthesis. Therefore, the establishment of highly enantioselective enzymatic synthesis of chiral 3-cyclohexene-1-carboxylic acid is of important application value.

At present, the methods for synthesizing chiral 3-cyclohexene-1-carboxylic acid mainly include Diels-Alder reaction, chemical resolution of racemic acids and enzymatic asymmetric hydrolytic resolution of 3-clohexene-1-carboxylate. The Diels-Alder reaction is currently the main method for the synthesis of chiral 3-cyclohexene-1-carboxylic acid. However, since butadiene is a gas, the product is not easy to separate, the reaction steps are cumbersome and the yield is low, further improvement is still needed (Synlett, 1990, 1, 38-39). The chemical resolution requires at least six recrystallization processes in acetone to separate the optically pure enantiomers, which leads to the large use of acetone. The resolution yield is only 20-30%, and the atom economy is low (Drugs & Clinic, 2013, 28, 126-128). It can be seen that the chemical synthesis of chiral 3-cyclohexene-1-carboxylic acid suffers many problems such as cumbersome operation, low yield and large use of acetone. The synthesis of chiral compounds by biocatalysis has the advantages of mild reaction conditions, high stereoselectivity, environmental friendliness, and convenient operation, making it an important method to replace or expand traditional chemical synthesis in sustainable development.

In 2004, Cihangir T et al. investigated the effects of porcine liver esterase PLE, horse liver esterase HLE and porcine pancreatic lipase PPL in the hydrolysis of racemic 3-cyclohexene-1-carboxylic acid methyl ester, and found that the product of hydrolysis with PLE and HLE is (S)-3-cyclohexene-1-carboxylic acid, ee>99% and 97% respectively; and the product of hydrolysis with PPL is (R)-3-cyclohexene-1-carboxylic acid, ee 91% (Tetrahedron Asymmetry, 2004, 15, 2057-2060). However, the above-mentioned enzymes are commercial enzymes derived from animals, and have the problems of high price, interference from isoenzymes, large differences between batches, and the risk of introducing viruses during practical use. In 2019, molecular modification of the carboxyesterase BioH derived from E. coli was performed by Xiafen Wu et al. to improve its enantioselectivity to (S)-3-cyclohexene-1-carboxylic acid methyl ester (Biosci. Biotechnol. Biochem., 2019, 83, 1263-1269). By the combined mutations reducing the steric hindrance and aromatic stacking, a mutant Mu3 (L24A/W81A/L209A) with higher S-selectivity was obtained, which can hydrolyze racemic-3-cyclohexene-1-carboxylic acid methyl ester with an ee of 32.3% to 70.9%. By further optimizing the reaction conditions, Mu3 can hydrolyze 40 mM substrate in a phosphate buffer (pH 8.0) containing 2.5% Tween 80 at 30° C., where the conversion rate is twice that of before optimization. Although the recombinase BioH has the activity of hydrolyzing 3-cyclohexene-1-carboxylic acid methyl ester, the enantioselectivity is low. In 2019, wild bacteria were screened by Dou Zhe et al. using 3-cyclohexene-1-carboxylic acid methyl ester as a substrate and it was found that Acinetobacter sp. JNU9335 can selectively hydrolyze the substrate to produce (S)-3-cyclohexene-1-carboxylic acid methyl ester which is hydrolyzed under an alkaline condition to obtain (S)-3-cyclohexene-1-carboxylic acid. 3.50 g (R,S)-3-cyclohexene-1-carboxylic acid methyl ester was added in a 50 mL reaction. After 12 hrs of reaction, the yield of the final product was 40%, and the $ee_s$ is 99% (Chinese Patent Application, Publication No.: CN 110272839 A).

Compared with traditional chemical synthesis, the biocatalytic method for producing chiral cyclohexene-1-carboxylic acid has the advantages of environmental friendliness, mild reaction conditions, and simple operation. However, the above method is currently restricted to the laboratory scale, and has the disadvantages of low enzyme activity, low product concentration, and long reaction time, thus being not suitable for industrial production. The preparation of chiral cyclohexene carboxylic acid by wild bacteria has the problems such as high enzyme load, causing high catalyst cost, serious emulsification of the reaction solution, and low yield. Therefore, there is a need to screen enzymes with high activity, good stability, high selectivity and ability to produce higher concentration of product in a short reaction time, to meet the needs in industrial production of chiral cyclohexene-1-carboxylic acid.

SUMMARY OF THE INVENTION

In view of the defects existing in the preparation of (S)-3-cyclohexene-1-carboxylic acid by enzymatic resolution in the prior art, the present invention provides a cyclohexenecarboxylate ester hydrolase with high catalytic activity, good enantioselectivity, and high tolerance to substrate and mutants thereof, a recombinant expression vector and recombinant expression transformant comprising a gene encoding the enzyme or a mutant thereof, a method for producing the recombinant enzyme, and a method for producing (S)-3-cyclohexene-1-carboxylic acid by resolution with the cyclohexenecarboxylate ester hydrolase.

A first object of the present invention is to provide a cyclohexenecarboxylate hydrolase, which is:
(a) a protein having an amino acid sequence as shown in SEQ ID NO:2; or
(b) a protein having an amino acid sequence modified from the amino acid sequence as shown in SEQ ID NO:2 by means of substitution, deletion, or addition of one or more amino acids, and having the activity of hydrolyzing 3-cyclohexene-1-carboxylate ester.

Preferably, the cyclohexenecarboxylate ester hydrolase is obtained by substituting the alanine residue at position 202 with a lysine residue, and the glycine residue at position 326 with an alanine residue in the amino acid sequence as shown in SEQ ID NO:2.

Preferably, the cyclohexenecarboxylate ester hydrolase is obtained by substituting the phenylalanine residue at position 78 with a valine reside, the alanine residue at position 202 with a lysine residue, and the glycine residue at position 326 with an alanine residue in the amino acid sequence as shown in SEQ ID NO:2.

A second object of the present invention is to provide a coding gene of the cyclohexenecarboxylate ester hydrolase.

A third object of the present invention is to provide a recombinant expression vector comprising the coding gene.

Preferably, the recombinant expression vector is constructed by ligating a nucleic acid sequence encoding the cyclohexenecarboxylate ester hydrolase or its mutant of the present invention to various suitable vectors by conventional methods in the art. The vector is preferably a plasmid, more preferably plasmid pET-28a(+). The gene encoding the cyclohexenecarboxylate ester hydrolase can be operatively linked to the downstream of a regulatory sequence suitable for expression to achieve the constitutive or inducible expression of the cyclohexenecarboxylate ester hydrolase.

A fourth object of the present invention is to provide a recombinant bacterium expressing the cyclohexenecarboxylate ester hydrolase.

Preferably, the recombinant bacterium is produced by transforming the recombinant expression vector of the present invention into a host cell. The host cell may be various conventional host cells in the art, provided that the recombinant expression vector can stably replicate by itself, and the carried cyclohexenecarboxylate ester hydrolase encoding gene can be effectively expressed. In the present invention, *Escherichia coli* is preferable, and *E. coli* BL21(DE3) or *E. coli* DH5α is more preferable.

A fifth object of the present invention is to provide use of the cyclohexenecarboxylate ester hydrolase in catalyzing methyl 3-cyclohexene-1-carboxylate to produce the optically active (S)-3-cyclohexene-1-carboxylic acid.

Preferably, (S)-3-cyclohexene-1-carboxylic acid is produced by catalyzing the enantioselective hydrolysis of methyl 3-cyclohexene-1-carboxylate in a buffer with the cyclohexenecarboxylate ester hydrolase to obtain (S)-3-cyclohexene-1-carboxylate, and then hydrolyzing (S)-3-cyclohexene-1-carboxylate by heating under an alkaline condition.

Preferably, the buffer is a citrate buffer, a phosphate buffer or a glycine-NaOH buffer, and the buffer has a pH of 5.0 to 10.0.

Preferably, the alkaline condition is a 0.5-1.5 M sodium hydroxide solution.

Preferably, the 3-cyclohexene-1-carboxylate ester is 3-cyclohexene-1-carboxylic acid methyl ester, 3-cyclohexene-1-carboxylic acid ethyl ester, 3-cyclohexene-1-carboxylic acid isopropyl ester or 3-cyclohexene-1-carboxylic acid butyl ester.

As compared with the prior art, the present invention has the following beneficial effects.

The cyclohexenecarboxylate ester hydrolase (AcEst1) and its mutants of the present invention can enantioselectively resolve methyl 3-cyclohexene-1-carboxylate with high efficiency to prepare optically active(S)-3-cyclohexene-1-carboxylic acid. When the substrate concentration is as high as 2000 mM (about 280 g/L), the optical purity of the product is higher than 99%, and the substrate/catalyst is as high as 3500 g/g. Compared with other preparation methods, the product prepared by the method of the present invention has high concentration and high optical purity, the catalytic efficiency is high, the reaction conditions are mild, and the present method is environmentally friendly, simple in operation and easy for industrial scale-up, thus having a good prospect of application in industry.

DETAILED DESCRIPTION OF THE PREFERRED EMBODIMENTS

Figure 1:
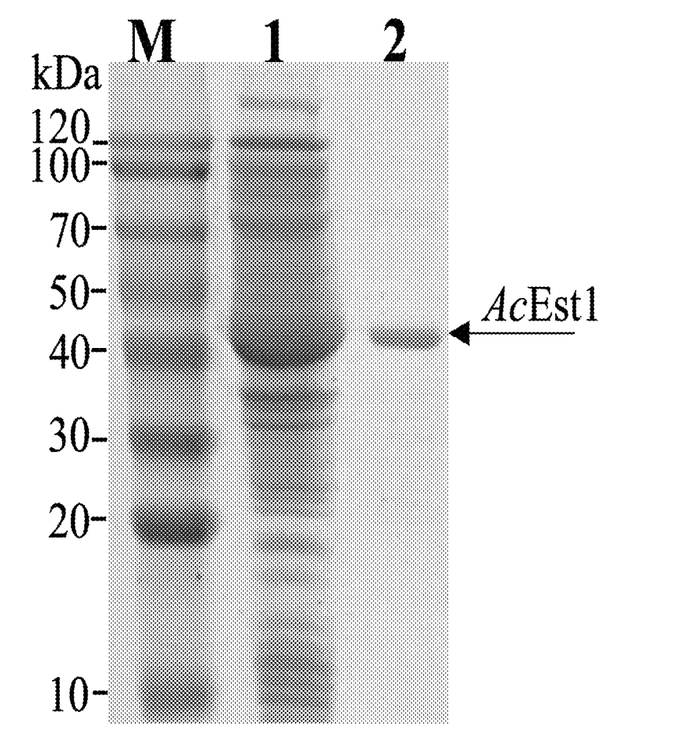
FIG. 1 shows the results of expression and purification of the cyclohexenecarboxylate ester hydrolase AcEst1, in which the bands from left to right are respectively standard protein marker, crude enzyme supernatant of AcEst1 and purified AcEst1 protein.

The present invention will be further described below with reference to the accompanying drawings and specific examples, so that those skilled in the art can better understand and implement the present invention; however, the present invention is not limited thereto.

Example 1: Cloning of Gene Encoding Cyclohexenecarboxylate Ester Hydrolase AcEst1

The strain *Acinetobacter* sp. JNU9335 was cultured in LB medium, and the high-purity, large-segment total genomic DNA was extracted by the CTAB (hexadecyltrimethylammonium bromide) method. An appropriate amount of *Acinetobacter* sp. JNU9335 was added to and frozen in liquid nitrogen, ground into powder, added with an appropriate amount of 2×CTAB extraction buffer (100 mmol/L Tris-HCl, pH 8.0, 20 mmol/L EDTA, 1.4 mol/L NaCl, 2% (w/v) CTAB, and 40 mmol/L mercaptoethanol), incubated at 65° C. for 10 min, and shaken intermittently. Then an equal volume of chloroform/isoamyl alcohol was added, mixed uniformly by gently turning upside down the centrifuge tube, and centrifuged at 8000 rpm for 10 min at room temperature. The supernatant was transferred to another centrifuge tube, and an equal volume of chloroform/isoamyl alcohol was added, mixed uniformly by gently turning upside down the centrifuge tube, and centrifuged at 8000 rpm for 10 min at room temperature. The upper aqueous phase was added to a new centrifuge tube, and an equal volume of isopropanol was added, mixed uniformly, and allowed to stand at room temperature for 30 min. The solution was centrifuged at 4000 rpm for 10 min, washed twice with 70% ethanol after the supernatant is removed, dried and added to 20 μL of TE buffer (100 mM Tris-HCl, 10 mM EDTA pH 8.0,) to dissolve the DNA, which was then stored at −20° C. for later use. Total DNA was partially enzymatically cleaved by Sau3AI, and the cleaved DNA fragments were purified by electrophoresis. Fragments of approximately 2-6 kb were recovered by a gel extraction kit, and the recovered DNA was dissolved in ddH$_2$O and stored at −20° C.

The DNA was connected to the vector pUC118 in the following reaction system:

TABLE 1

Ligation reaction system

| Reagent | Amount |
| --- | --- |
| pUC118(BamHI/BAP) | 0.1 µg |
| Cleaved total DNA fragment | 0.1 µg |
| 10 × ligase buffer | 1.0 µL |
| T$_4$ DNA ligase | 0.5 µL |
| Adding ddH$_2$O to | 10.0 µL |

After incubation at 16° C. for 12 h, 10 µL of the enzymatic ligation product was transformed into 200 µL of E. coli DH5α competent cells. The obtained recombinant was induced to express, and then the substrate 3-cyclohexene-1-carboxylic acid methyl ester was added for reaction. Where the product 3-cyclohexene-1-carboxylic acid was produced, high-throughput screening was carried out based on the color changes of bromothymol blue-phenol red dual indicators at different pH values. The colonies with obvious color changes, that is, the colonies changing from brownish green to yellow were further screened, and the product was detected by HPLC. The recombinant with an obvious product peak was shipped to Tianlin Biotechnology Co., Ltd. for sequencing. A nucleotide sequence as shown in SEQ ID NO:1 was obtained. The amino acid sequence deduced from the nucleotide sequence is as shown in SEQ ID NO:2, and the cyclohexenecarboxylate ester hydrolase expressed by this sequence is designated as AcEst1.

Example 2: Production of Recombinant Plasmid and Bacterium Comprising AcEst1, and Recombinant Hydrolase Using the forward primer 5'-gtgccgcgcggcagccatat-gATGGGCGTGTTGAATCAAACTT-3' (SEQ ID NO:3) and reverse primer 5'-gtggtggtggtggtgctcgagTTA-TTTGG-CATTCTTATCCCAAAA-3' (SEQ ID NO:4), the nucleotide sequence of AcEst1 obtained in Example 1 was amplified by polymerase chain reaction, and the obtained DNA fragment containing the AcEst1 sequence was cleaved with NdeI and XhoI respectively, and then ligated to the plasmid pET-28a (+) that was also cleaved with NdeI and XhoI, to obtain the recombinant plasmid pET-28a(+)-AcEst1.

The obtained recombinant plasmid pET-28a(+)-AcEst1 was transformed into E. coli BL21, to construct recombinant E. coli containing the cyclohexenecarboxylate ester hydrolase AcEst1. The constructed recombinant E. coli was inoculated into LB medium (peptone 10 g/L, yeast extract 5 g/L, NaCl 10 g/L, pH 7.0) containing 50 µg/mL kanamycin, and incubated overnight at 37° C. with shaking. The cells were inoculated to a 2 L conical flask containing 600 mL LB medium in an amount of 1% (v/v), and incubated on a shaker at 37° C. and 180 rpm. When the OD$_{600}$ of the culture medium reached 0.6-2.0, IPTG with a final concentration of 0.2 mmol/L was added as an inducer. After induction at 16° C. for 16 h, the culture medium was centrifuged, and the cells were collected and washed twice with saline to obtain resting cells. The obtained resting cells were suspended in Tris-HCl buffer (20 mM, pH 8.0), homogenized by a high-pressure homogenizer, and freeze-dried to obtain recombinant AcEst1.

Example 3: Production of Mutant A202K/G326

Mutant A202K/G326A is a random mutant. A random mutant library of AcEst1 was established by error-prone PCR, and the color change of the indicator at different pH values described in Example 1 was used as a means of high-throughput screening. The terminal primers were designed: the forward primer 5'-gtgccgcgcggcagccatat-gATGGGCGTGTTGAATCAAACTT-3' (SEQ ID NO:5) and the reverse primer 5'-gtggtggtggtggtgctcgagTTAT-TTGGCATTCTTATCCCAAAA-3' (SEQ ID NO:6). PCR system (50 µL): rTaq polymerase 0.25 µL, 10×rTaq Buffer 5 µL, dNTP 5 µL, MgSO$_4$ 2 µL, template plasmid about 100 ng, forward primer 2 µL, reverse primer 2 µL, MnCl$_2$ (10 mM) 0.5 µL, and ddH$_2$O making up to 50 µL.

PCR reaction procedure: (1) pre-denaturation at 98° C. for 5 min; 30 cycles of (2) denaturation at 98° C. for 30 s, (3) annealing at 55° C. for 30 s, and (4) extension at 72° C. for 1 min; and final extension at 72° C. for 10 min. The PCR product was stored at −20° C.

The PCR fragment containing random mutation sites was cleaved with NdeI and XhoI, then ligated to the pET-28a(+) plasmid with the same cleavage sites, and then transformed into E. coli BL21 (DE3) competent cells. The cells were coated evenly on an LB agar plate containing 50 µg/mL kanamycin. After culturing overnight at 37° C., monoclones were picked to a deep-well plate for culture and induced expression. The mutant library was screened for activity according to the color change of the pH indicator and a mutant with increased activity was obtained, which was shipped to Tianlin Biotechnology Co., Ltd. for sequencing. The sequencing result was aligned with the sequence of the cyclohexenecarboxylate ester hydrolase (AcEst1) gene by the DNAMAN software. The result shows that the alanine at position 202 is mutated to lysine and the glycine at position 326 is mutated to alanine. The obtained mutant is designated as A202K/G326A.

The mutant protein A202K/G326A obtained by substituting the alanine residue at position 202 with a lysine residue, and the glycine residue at position 326 with an alanine residue in the amino acid sequence as shown in SEQ ID NO:2 has a 3-time increased activity for hydrolyzing 3-cyclohexene-1-carboxylic acid methyl ester. For the same substrate concentration, the mutant A202K/G326A can achieve a conversion rate similar to that of WT only after reaction for 2 h, where the reaction time is shortened by 3 times.

Example 4: Production of Plasmid, Recombinant Bacterium and Mutant A202K/G326A

The plasmid pET-28a(+)-A202K/G326A obtained in Example 3 was extracted, and transformed into E. coli BL21. The E. coli cells were inoculated into LB medium (peptone 10 g/L, yeast extract 5 g/L, NaCl 10 g/L, pH 7.0) containing 50 µg/mL kanamycin, and incubated overnight at 37° C. with shaking. The cells were inoculated to a 2 L conical flask containing 600 mL LB medium in an amount of 1% (v/v), and incubated on a shaker at 37° C. and 180 rpm. When the OD$_{600}$ of the culture medium reached 0.6-2.0, IPTG with a final concentration of 0.2 mmol/L was added as an inducer. After induction at 16° C. for 16 h, the culture medium was centrifuged, and the cells were collected and washed twice with saline to obtain resting cells. The obtained resting cells were suspended in Tris-HCl buffer (20 mM, pH 8.0), homogenized by a high-pressure homogenizer, and freeze-dried to obtain mutant A202K/G326A.

Example 5: Production of Mutant F78V/A202K/G326A

A202K/G326A was subjected to site-directed mutagenesis, as described in the Site-Directed Mutagenesis Kit (Stratagene, Catalog #200522).

Degenerate primers F: 5'-TCGCGTAAATTGNDTGAT-CATCAAATT-3' (SEQ ID NO:7), and R: 5'-AATTTGAT-GATCAHNCAATTTACGCGA-3' (SEQ ID NO:8) were designed, where N represents a combination of four bases A, T, C, and G; D represents a combination of three bases A, G, and T; and H represents a combination of three bases A, C, and T.

PCR reaction system (50 μL): KOD plus Neo 0.25 μL, template 0.5-20 ng, 5 μL 10×KOD plus Neo buffer, 5 μL dNTP (each 2.0 mM), 2 μL MgSO$_4$ (25 mM), forward primer 2 μL, reverse primer 2 μL, and ddH$_2$O making up to 50 μL.

The template was the plasmid pET-28a(+)-A202K/G326A comprising the cyclohexenecarboxylate ester hydrolase mutant obtained in Example 3.

PCR reaction procedure: (1) pre-denaturation at 98° C. for 5 min; 20 cycles of (2) denaturation at 98° C. for 30 s, (3) annealing at 55° C. for 30 s, and (4) extension at 68° C. for 3.5 min; and final extension at 68° C. for 10 min. The PCR product was stored at −20° C.

The amplified PCR product was digested with endonuclease DpnI for 2 h at 37° C. and transformed into *E. coli* BL21 competent cells. Then, the cells were evenly coated on an LB agar plate containing 50 μg/mL kanamycin. After culturing overnight at 37° C., 200 monoclones were picked to a deep-well plate for culture and induced expression. The mutant library was screened for activity according to the color change of the pH indicator and a mutant with increased activity was obtained, which was shipped to Tianlin Biotechnology Co., Ltd. for sequencing. The sequencing result was aligned with the sequence of the cyclohexenecarboxylate ester hydrolase (AcEst1) gene by the DNAMAN software. The result shows that the position 78 is mutated to valine, the position 202 is mutated to lysine and the position 326 is mutated to alanine. The obtained mutant is designated as F78V/A202K/G326A.

The mutant protein F78V/A202K/G326A obtained by substituting the phenylalanine residue at position 78 with a valine residue, the alanine residue at position 202 with a lysine residue, and the glycine residue at position 326 with an alanine residue in the amino acid sequence as shown in SEQ ID NO:2 has a 6-time increased activity for hydrolyzing 3-cyclohexene-1-carboxylic acid methyl ester. For the same substrate concentration, the mutant F78V/A202K/G326A can achieve a conversion rate similar to that of WT only after reaction for 1 h, where the reaction time is shortened by 6 times.

Example 6: Production of Plasmid and Recombinant Bacterium Comprising Mutant F78V/A202K/G326A, and Recombinant Hydrolase The plasmid pET-28a(+)-F78V/A202K/G326A obtained in Example 5 was extracted, and transformed into *E. coli* BL21. The *E. coli* cells were inoculated into LB medium (peptone 10 g/L, yeast extract 5 g/L, NaCl 10 g/L, pH 7.0) containing 50 jug/mL kanamycin, and incubated overnight at 37° C. with shaking. The cells were inoculated to a 2 L conical flask containing 600 mL LB medium in an amount of 1% (v/v), and incubated on a shaker at 37° C. and 180 rpm. When the OD$_{600}$ of the culture medium reached 0.6-2.0, IPTG with a final concentration of 0.2 mmol/L was added as an inducer. After induction at 16° C. for 16 h, the culture medium was centrifuged, and the cells were collected and washed twice with saline to obtain resting cells. The obtained resting cells were suspended in Tris-HCl buffer (20 mM, pH 8.0), homogenized by a high-pressure homogenizer, and freeze-dried to obtain mutant F78V/A202K/G326A.

Example 7: Catalytic Performance of Recombinant AcEst1

The cyclohexenecarboxylate ester hydrolase of the present invention was used in the production of optically active (S)-3-cyclohexene-1-carboxylic acid by enzymatic hydrolysis of racemic methyl 3-cyclohexene-1-carboxylate.

At different temperatures (20-65° C.), sodium phosphate (100 mM, pH 7.0) was used as a buffer, and 1 mM p-nitrophenol cyclohexenecarboxylate was used as a substrate for activity determination. According to the change of absorbance at 405 nm, the activity of the cyclohexenecarboxylate hydrolase AcEst1 was investigated. The results are shown in Table 2. AcEst1 has the highest catalytic activity at 40° C. When the temperature continues to rise, the enzyme activity begins to decrease.

TABLE 2

Activity of cyclohexenecarboxylate ester hydrolase AcEst1 at different temperatures

| Temperature (° C.) | Relative activity (%) |
|---|---|
| 20 | 40.9 ± 0.2 |
| 25 | 58.2 ± 0.5 |
| 30 | 73.7 ± 0.6 |
| 35 | 86.9 ± 0.8 |
| 40 | 100.0 ± 0.3 |
| 45 | 97.1 ± 0.7 |
| 50 | 86.6 ± 0.4 |
| 55 | 78.8 ± 0.2 |
| 60 | 71.4 ± 0.2 |
| 65 | 67.8 ± 0.3 |

When the reaction temperature was 30° C., 1 mM p-nitrophenol cyclohexenecarboxylate was used as a substrate for activity determination. The activity of AcEst1 in buffers with different pH values was investigated according to the change of absorbance at 405 nm. The buffer systems used: sodium citrate buffer (pH 5.0-6.0); sodium phosphate buffer (pH 6.0-8.0); Tris-HCl buffer (pH 8.0-9.0) and glycine-NaOH buffer (pH 9.0-10.0). The results are shown in Table 3. The optimum pH for AcEst1 is pH 9.0 (Tris-HCl buffer).

TABLE 3

Activity of the cyclohexenecarboxylate ester hydrolase AcEst1 in buffers with different pH values

| Buffer | pH | Relative activity (%) |
|---|---|---|
| Sodium citrate | 4.0 | 0.1 ± 0.02 |
| | 5.0 | 0.2 ± 0.01 |
| | 6.0 | 0.6 ± 0.05 |

TABLE 3-continued

Activity of the cyclohexenecarboxylate ester hydrolase AcEst1 in buffers with different pH values

| Buffer | pH | Relative activity (%) |
|---|---|---|
| Sodium phosphate | 6.0 | 0.8 ± 0.1 |
|  | 7.0 | 36.3 ± 1.2 |
|  | 8.0 | 85.5 ± 2.6 |
| Tris-HCl | 8.0 | 95.0 ± 1.7 |
|  | 9.0 | 100.0 ± 2.1 |
| Glycine-NaOH | 9.0 | 96.5 ± 2.3 |
|  | 10.0 | 78.2 ± 3.2 |

Example 8: Catalytic Hydrolytic Resolution of Various 3-Cyclohexene-1-Carboxylate Esters by the Recombinant AcESt1

Recombinant AcEst1 can catalyze the enantioselective hydrolysis of various 3-cyclohexene-1-carboxylate esters to produce (S)-3-cyclohexene-1-carboxylic acid with high optical purity. The activities of AcEst1 for 3-cyclohexene-1-carboxylic acid methyl ester, 3-cyclohexene-1-carboxylic acid ethyl ester, 3-cyclohexene-1-carboxylic acid isopropyl ester and 3-cyclohexene-1-carboxylic acid butyl ester and the optical purity of the hydrolysis products were investigated respectively. The wild-type AcEst1 obtained in Example 3 was used to catalyze the hydrolysis of different 3-cyclohexene-1-carboxylate esters. 5 mg of crude recombinant AcEst1 enzyme powder was weighed, dissolved in 10 mL of Tris-HCl buffer (200 mM, pH 9.0), added to the substrate 3-cyclohexene-1-carboxylate esters to give a final concentration of 50 mM, and reacted at 30° C. The results are shown in Table 4.

TABLE 4

The activity of AcEst1 for different 3-cyclohexene-1-carboxylate esters and optical purity of the products

| Substrate | Reaction time (h) | Conversion rate (%) | $ee_s$ (%) | $ee_p$ (%) |
|---|---|---|---|---|
| 3-cyclohexene-1-carboxylic acid methyl ester | 6 | 49 | 73 | 71 |
| 3-cyclohexene-1-carboxylic acid ethyl ester | 6 | 47 | 64 | 56 |
| 3-cyclohexene-1-carboxylic acid isopropyl ester | 10 | 47 | 66 | 59 |
| 3-cyclohexene-1-carboxylic acid butyl ester | 16 | 49 | 19 | 18 |

Example 9: Catalytic Hydrolytic Resolution of 3-Cyclohexene-1-Carboxylic Acid Methyl Ester by Recombinant AcEst1

The typical enzymatic hydrolysis and resolution of 3-cyclohexene-1-carboxylate ester was as follows. 16 mg of freeze-dried recombinant AcEst1 enzyme powder was dissolved in 200 mL of Tris-HCl buffer (200 mM, pH 9.0), and added to the substrate 3-cyclohexene-1-carboxylic acid methyl ester to give a final concentration of 200-2000 mM (28-280 g/L), where the corresponding S/C was 350-3500 g/g. The reaction was performed at 30° C. with mechanical stirring at 200 rpm, and the pH was controlled at 9.0 by adding 1.0 M $Na_2CO_3$, until the e.e. of the substrate was >99%. After the reaction, the pH was adjusted to 12 with 2 M NaOH, and then the solution was extracted three times with dichloromethane. The extracts were combined and dried overnight over anhydrous sodium sulfate. (S)-3-cyclohexene-1-carboxylic acid methyl ester was obtained by removing the solvent by rotary evaporation. The conversion rate and the e.e. value of the hydrolysis product were determined by gas chromatography (chiral capillary column B-DM) Specific analysis conditions: $N_2$ as carrier gas, inlet temperature 280° C., detector temperature 280° C., initial column temperature 50° C., 2° C./min to 100° C. for 10 min. The results are shown in Table 5. Then (S)-3-cyclohexene-1-carboxylic acid methyl ester was added to 1 M NaOH aqueous solution, reacted for 6 h with stirring under reflux at 50° C., adjusted to pH 5.0 by adding 1 M HCl aqueous solution, and extracted 3 times with an equal volume of dichloromethane. The organic layers were combined, dried over anhydrous $Na_2SO_4$, filtered, and dried by rotary evaporation to obtain (S)-3-cyclohexene-1-carboxylic acid. The resulting product is a liquid with a special odor. The total yield after separation is 38%, and the optical purity is 99% e.e.

TABLE 5

Results of catalyzing asymmetric resolution of 3-cyclohexene-1-carboxylic acid methyl ester by recombinant AcEst1

| Substrate concentration (mM) | Reaction time (h) | Conversion rate (%) | $ee_s$ (%)/(conformation) |
|---|---|---|---|
| 200 | 8 | 61.5 | 99 |
| 500 | 8 | 62.8 | 99 |
| 1000 | 9 | 62.8 | 99 |
| 2000 | 20 | 61.9 | 99 |

Example 10: Catalyzing Hydrolytic Resolution of 3-Cyclohexene-1-Carboxylate Methyl Ester by AcEst1 and Mutants Thereof The wild-type AcEst1 obtained in Example 3, the mutant A202K/G326A obtained in Example 4, and the mutant F78V/A202K/G326A obtained in Example 5 were respectively used to catalyze the hydrolysis of 3-cyclohexene-1-carboxylic acid methyl ester. 5 mg of crude recombinant AcEst1 or mutant enzyme powder was weighed, dissolved in 10 mL of Tris-HCl buffer (200 mM, pH 9.0), added to the substrate 3-cyclohexene-1-carboxylate to give a final concentration of 50 mM, and reacted at 30° C. From the reaction (as shown in Table 6), it can be seen that the time required for the mutant to achieve a conversion rate of about 50% is significantly reduced.

TABLE 6

Results of catalyzing asymmetric resolution of 3-cyclohexene-1-carboxylate methyl ester by recombinant AcEst1 and mutants thereof

| Enzyme | Reaction time (h) | Conversion rate (%) | $ee_s$ (%)/(conformation) |
|---|---|---|---|
| AcEst1 | 6 | 47.2 | 75.3/(S) |
| A202K/G326A | 2 | 49.3 | 73.9/(S) |
| F78V/A202K/G326A | 1 | 46.8 | 76.6/(S) |

Example 11: Production of (S)-3-Cyclohexene-1-Carboxylic Acid

The reaction was carried out in a 1 L three-necked flask. 200 mL of Tris-HCl buffer at pH 9.0, 16 mg of crude F78V/A202K/G326A enzyme powder prepared in Example 5, and 58.7 g of racemic 3-cyclohexene-1-carboxylic acid methyl ester were added, and reacted at 30° C. under mechanical stirring at 200 rpm, during which 1 M $Na_2CO_3$ was added by fed-batch to maintain the pH of the reaction solution at 9.0. After reaction for 12 h, the conversion rate reached 61.1%, and the optical purity of (S)-3-cyclohexene-1-carboxylic acid methyl ester was >99%. After the reaction, the pH was adjusted to 12 with 2 M NaOH, and then the solution was extracted three times with dichloromethane. The extracts were combined and dried overnight over anhydrous $Na_2SO_4$. (S)-3-cyclohexene-1-carboxylic acid methyl ester was obtained by removing the solvent by rotary evaporation. Then (S)-3-cyclohexene-1-carboxylic acid methyl ester was added to 1 M NaOH aqueous solution, reacted for 6 h with stirring under reflux at 50° C., adjusted to pH 5.0 by adding 1 M HCl aqueous solution, and extracted 3 times with an equal volume of dichloromethane. The organic layers were combined, dried over anhydrous $Na_2SO_4$, filtered, and dried by rotary evaporation to obtain (S)-3-cyclohexene-1-carboxylic acid (22.3 g, yield 38%, GC purity 99.0%, and optical purity 99.5% e.e).

The above-described embodiments are merely preferred embodiments for the purpose of fully illustrating the present invention, and the scope of the present invention is not limited thereto. Equivalent substitutions or modifications can be made by those skilled in the art based on the present invention, which are within the scope of the present invention. The scope of the present invention is defined by the appended claims.

What is claimed is:

1. A cyclohexenecarboxylate ester hydrolase, wherein the hydrolase is a protein having an amino acid sequence modified from the amino acid sequence as shown in SEO ID NO: 2 and having the activity of hydrolyzing methyl 3-cyclohexene-1-carboxylate, wherein the modified protein is obtained by:
   (a) substituting the alanine residue at position 202 with a lysine residue, and the glycine residue at position 326 with an alanine residue in the amino acid sequence as shown in SEO ID NO: 2, or
   (b) substituting the phenylalanine residue at position 78 with a valine reside, the alanine residue at position 202 with a lysine residue, and the glycine residue at position 326 with an alanine residue in the amino acid sequence as shown in SEO ID NO: 2.

2. A gene encoding the cyclohexenecarboxylate ester hydrolase according to claim 1.

3. A recombinant expression vector, comprising the gene according to claim 2.

4. A recombinant bacterium expressing the cyclohexenecarboxylate ester hydrolase according to claim 1.

5. A method of catalyzing methyl 3-cyclohexene-1-carboxylate to produce optically active(S)-3-cyclohexene-1-carboxylic acid, comprising:
   providing a cyclohexenecarboxylate ester hydrolase, wherein the hydrolase is:
   (a) a protein having an amino acid sequence as shown in SEO ID NO: 2; or
   (b) a protein having an amino acid sequence modified from the amino acid sequence as shown in SEO ID NO: 2 and having the activity of hydrolyzing methyl 3-cyclohexene-1-carboxylate, wherein the modified protein is obtained by substituting the alanine residue at position 202 with a lysine residue, and the glycine residue at position 326 with an alanine residue in the amino acid sequence as shown in SEO ID NO: 2, or the hydrolase is obtained by substituting the phenylalanine residue at position 78 with a valine reside, the alanine residue at position 202 with a lysine residue, and the glycine residue at position 326 with an alanine residue in the amino acid sequence as shown in SEO ID NO: 2; and
   hydrolyzing methyl 3-cyclohexene-1-carboxylate in the presence of the hydrolase to produce optically active (S)-3-cyclohexene-1-carboxylic acid.

6. The method according to claim 5, wherein hydrolyzing methyl 3-cyclohexene-1-carboxylate comprises placing methyl 3-cyclohexene-1-carboxylate and the hydrolase in a buffer, and heating the buffer under an alkaline condition.

7. The method according to claim 6, wherein the buffer is a citrate buffer, a phosphate buffer, or a glycine-NaOH buffer, and the buffer has a pH of 5.0 to 10.0.

8. The method according to claim 6, wherein the alkaline condition is obtained by adding 0.5 to 1.5 M sodium hydroxide solution to the buffer comprising the methyl-3-cyclohexene-1-carboxylate and the hydrolase.

* * * * *